United States Patent [19]

Liu

[11] Patent Number: 4,945,115

[45] Date of Patent: Jul. 31, 1990

[54] PROCESS FOR PREPARING FERULIC ACID

[76] Inventor: Yaguang Liu, 30 Seaman Ave., New York, N.Y. 10034

[21] Appl. No.: 63,433

[22] Filed: Jun. 18, 1987

Related U.S. Application Data

[62] Division of Ser. No. 732,146, May 9, 1985, Pat. No. 4,687,761.

[51] Int. Cl.$^5$ .............................................. A61K 31/05
[52] U.S. Cl. ..................................................... 514/731
[58] Field of Search ........................................ 514/731

[56] References Cited

PUBLICATIONS

Merck Index, No. 3986, 9th Ed., p. 528, 1976.
Chem. Abst. H. J. Klosterman et al., 54:557e, 1960.

Primary Examiner—John W. Rollins
Attorney, Agent, or Firm—Chenpatents

[57] ABSTRACT

A new pharmaceutical composition for treatment and prevention of side effects of anticancer chemotherapy and radiotherapy and increasing the immune function contains Ferulic acid, Ginsenoside, Anethole and sodium Cinnamate. Processes for producing these components and related pharmacological effect are provided.

4 Claims, No Drawings

PROCESS FOR PREPARING FERULIC ACID

This application is a division of application Ser. No. 732,146, filed on May 9, 1985, now U.S. Pat. No. 4,687,761.

BACKGROUND OF THE INVENTION

1. Field of the Invention

This invention relates to a new pharmaceutical composition for decreasing side effects of anticancer chemotherapy and increasing the immune function in human body.

Specifically, this invention provides a new composition of four major active ingredients.
- A. Ferulic acid extracted from Levisticum Officinale Koch or Angelica sinensis Diels.
- B. Ginsenoside extracted from Panax quinquefolium L. or Panax ginseng C. A. Mey.
- C. Anethole extracted from Foeniculum Vulgare Mill.
- D. Sodium cinnamate extracted from Cinnamomum Cassia Blume or Cinnamomum Cassia Presl.

Four herbs: Levisticum Officinale, Foeniculum Vulgare Mill, Panax quinquefolium L or Panax ginseng C. A. Mey and Cinnamomum Cassia Blume are regarded by F.D.A. of U.S. as recognized as safe.

2. Description of Prior Art

A lot of anticancer medicine including chemical and antibiotics have effect to kill off cancer cells. But it also kills off some normal human cells. For example, Cyclophosphamide is a chemotherapeutic drug which is highly effective against a wide range of human cancers. Cyclophosphamide established a role in the treatment of some major cancer types including Lymphomas, Acute Lymphatic Leukemias, Chronic Lymphatic Leukemias, Breast, Pulmonal, Ovarial cancer and Tumor of marrow mulciple, Osseous, Sarcoma, etc. Unfortunately, Cyclophosphamide has toxicity, for example, it does damage to hemotopoietic organs, alimentary tract and decreasing immune function. The toxicity of other anticancer medicine, for example, Fluorouracil, Mustine and 6-Mercaptopurine, etc. is higher than Cyclophosphamide.

Some antibiotics are effective anticancer drugs, for example, Adriamycin is used for treatment of some cancers which include leukemias, gastric pancreatic, breast cancer, etc. A prime limiting factor to the administration of adriamycin is cardiotoxicity. The most serious side effect of adriamycin administration is myocardial degeneration causing congestive heart failure. This acute cardiomyopathy may manifest pericarditis-myocarditis, acute left ventricular dysfunction, arrhythmia and myocardial infarction. Adriamycin induced cardiomyopathy was thought to be permanent and rapidly progressive. Late cardiomyopathy develops in weeks, months or even years. Some patients were reported to have developed progressive cardiomyopathy two and two-half years after receiving this drug.

Obviously, to overcome toxicity of anticancer is very important. Many agents have been suggested to reduce or prevent toxicity of anticancer midicine. For example, Vitamin E and N-acetyl-L-Cysteine have also been reported to be effective in preventing adriamycin cardiotoxicity. Although more recent research showed evidence to contradict these findings, in that neither of vitamin E and N-acetyl-L-Cysteine prevents adriamycin-induced cardiotoxicity.

So far, no drugs have been succeeded to overcome toxicity of anticancer drugs.

The basics of research of decreasing side effect in radiationtherapy are the same as in chemotherapy.

For reasons given above, effective treatment of cancer is very much hampered.

SUMMARY OF INVENTION

There is a need to provide a composition comprising several active ingredients which, in combination, are useful in treating and preventing toxicity of anticancer drugs in human body and in increasing immune function. This invention provides a pharmaceutical composition referred to as PDI.

PDI comprises (A) Ferulic Acid, (B) Ginsenoside, (C) Anethole, (D) Sodium Cinnamate. The composition of PDI and the sources of its components are listed below:

TABLE 1

| | Component | Source |
|---|---|---|
| (A) | Ferulic Acid | Roots of *Levisticum Officinale* Koch or Angelica Sinensis Diels |
| (B) | Ginsenoside | Roots of *Panax quinquefolium* L or *Panax ginseng* C. A. Mey, |
| (C) | Anethole | Fruits of *Foeniculum Vulgare* Mill |
| (D) | Sodium Cinnamate | Stem of *Cinnamomum Cassia* Blume or *Cinnamomum Cassia* Presl |

The process for producing PDI comprises separately extracting ground of the above natural materials with appropriate solvents such as alcohol or water, removing lipids by extraction with ether or petroleum ether, crystalization or chromatographic fractionation and then mixing its components in the desired preportion.

The chemical structures of the components of PDI are shown in Formulae I–V

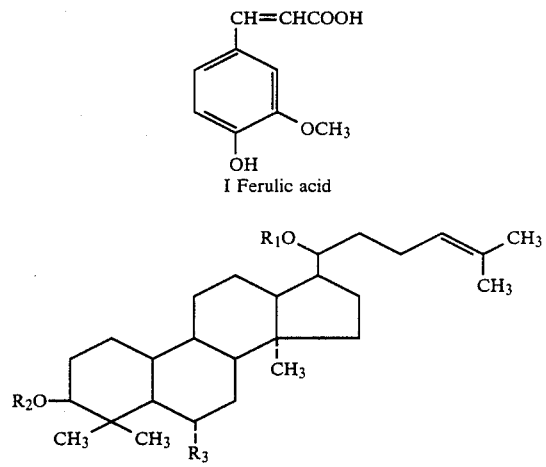

When
$R_1$ = Glucose $\underline{6\ 1}$ Glucose
$R_2$ = Glucose $\underline{2\ 1}$ Glucose
$R_3$ = H
The compound is Ginsenoside $b_1$.
Melting point, 198°–202° C.
When
$R_1$ = Glucose
$R_2$ = H
$R_3$ = —O—Glucose
The compound is Ginsenoside $g_1$.

Melting point, 192°-194° C.

II Chemical structure of Ginsenoside.

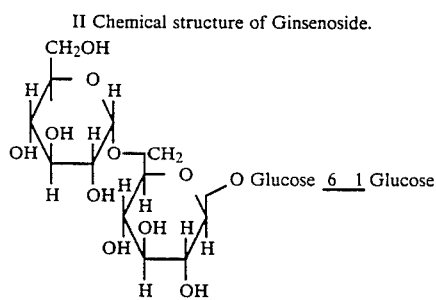

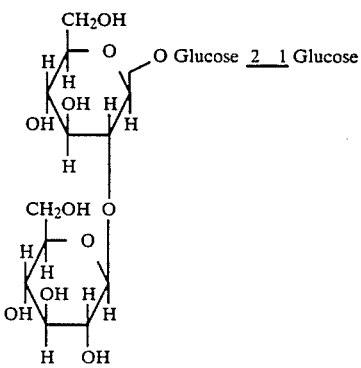

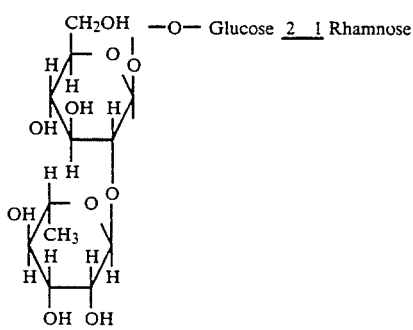

III chemical structure of substituents
of Ginsenoside

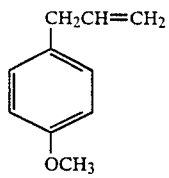

IV chemical structure of substituents
of Anethole

V chemical structure of substituents
of Sodium Cinnamate

DETAILED DESCRIPTION

The invention is further illustrated by the following examples and tests but not limited by the following examples:

EXAMPLE 1

Ferulic acid extracted from Levisticum Officinale Koch or Angelica sinensis diels 1 kg of dried powder of Levisticum Officinale Koch or Angelica sinensis Diels is extracted with 5000 ml of boiling water for 1 hour. Repeat 3 times. Combine extractives. Distilled to 1000 ml by reduced pressure distillation (about 17 mm Hg is better). Add 2000 ml 95% ethanol to 1000 ml the residue with stirring. Set 24 hours. Pour filter. Save the filtrate. Filtrate is concentrated to syrup under reduced pressure distillation (about 17 mm Hg absolute). Add 300 g silica gel to syrup. Cool the syrup gel mixture to room temperature and dry the same at 60° C. Dried powders is placed in a percolator. These powders are washed with 95% ethanol until ethanol become light color. Ethanol is combined and distilled at 17 mm Hg. Ethanol is recovered and a still residue is obtained. This still residue is dissolved in 200 ml of distilled water. This water solution is mixed with polyamide. Set column. Wash with distilled water, then wash with 50% ethanol. 50% ethanol is combined and distilled at 17 mm Hg. The residue is dissolved in 100 ml of methanol. This methanol is mixed with 5 g silica gel. Dried. Pass the resulting methanol solution through the column (4×22 cm). Wash column with benzol-acetone (7:3). The benzol-acetone is combined and distilled at 17 mm Hg. Crystals are obtained. Crystals crystalized again in chloroform-methanol (1:1). White crystals are obtained.

Melting point is 169.5°-171° C. Yield is about 0.1%.

EXAMPLE 2

Extraction and Purification of Ginsenoside 1000 gms. of dried ginseng powder is extracted with 2000 ml of 95% ethanol at room temperature for 24 hours. The powder is recovered by filtration. filtrate A is saved and the powder filtercake is refluxed with an additional 2000 ml of 95% ethanol on a steam bath. the mixture is filtered again. Filtrate B is saved and the powder filtercake is refluxed two more times for 6 hours with additional 2000 ml batches at 95% ethanol and filtered, providing filtrates C and D. Filtrates A,B,C, and D are combined and distilled at 17 mm Hg absolute, whereby ethanol is recovered and a still residue is obtained.

This still residue is dissolved in 500 ml of distilled water. This water solution is extracted five times with 500 ml of a lipophilic solvent, e.g. diethyl ether or petroleum ether, whereby lipids are removed from the solution.

To this acqueous raffinate is added 500 ml of water-saturated n-butanol and the mixture is distilled at 17 mm Hg absolute to dryness, wereby a powder residue is obtained. This powder is dissolved in 500 ml of anhydrous ethanol, and 2000 ml of acetone are added with agitation while a precipitate forms. The precipitate is recovered by filtration and washed twice with acetone and twice with diethyl ether and dried. About 60 gms. of a white to light yellow powder are recovered. This is Ginsenoside.

EXAMPLE 3

Anethole (p-allyl-methoxy benzene) extracted from Fennel (Foeniculum Vulgare Mill)

1 kg Fennel oil is Fractional-distilled over an oil bath in distillation apparatus. Collecting distillate at 229°–237° C. The resulting light-yellow liquor is anethole. $d_{25}^{25} 0.983–0.987$. Refractive index $n_D^{25} 1.588–1.561$ Yield is 60%.

EXAMPLE 4

Sodium Cinnamate

The Sodium Cinnamate are already on sale in the market. The sodium Cinnamate which extracted from Cinnamomum Cassia Blume or Cinnamomum Cassia Presl is expensive.

EXAMPLE 5

Preparation of PDI

On a dry basis, the composition of PDI may vary as follows:

TABLE 2

|  | Weight percent | Preferred composition weight percent |
|---|---|---|
| Ferulic acid | 15–60 | 25 |
| Ginsenoside | 5–50 | 20 |
| Anethole | 20–65 | 30 |
| Sodium Cinnamate | 15–60 | 25 |

The dry ingredients of PDI, prepared in accordance with the present invention, may be incorporated in tablets, capsules and syrups by conventional methods.

Each oral dose for an adult is 20 mg (20–200 mg) injected dose for an adult is 10 mg (5–50 mg).

This invention will now be described with reference to its beneficial effects, as illustrated by the following tests:

EXAMPLE 6

The influence of PDI on the survival rate of myocardial cell

Materials and methods

Hearts were removed from 11 days embryos and were dissociated at 37° C. for 45 minutes with 0.25% trypsin (sigma, type III), 0.025% collagenase (sigma, type I), and 0.005% pancreatin(NBCo) prepared in calcium and magnesium free saline G containing 4% chicken serum. Then the tissue is dispersed into a single cell suspension in culture medium containing 5 g/ml DNAse I(sigma). Viable cell counts were determined by hemocytometer counting. Cells were dispersed into 60 mm culture disher (surface area 2000 mm$^2$) at densities of 200 cells/mm$^2$.

Culture were maintained in Ham's F-12K cln$^-$ modified by Clark [1981] and supplemented with 5% fetal bovine serum, gentamicin (5 mg/100 ml). Tissue culture plates were incubated under at constant 5% $CO_2$ and 95% air at 37° C.

Cells counted—all cells were counted in 20 randomly selected fields across the entire dish. A Zeiss microscope 25× objective having a field of view of 0.32 mm$^2$ was used for cell counting.

Immunostaining

I. Reagents

1. CMF solution: 8.0 g NaCl, 0.4 g KCl, 0.15 g $KH_2PO_4$, $0.29Na_2HPO_4.7H_2O$, 1000 ml distilled water, solution is sterilized by passage through a 0.22 milliopore.
2. Phosphat-buffered saline(PBS): 10 ml 1M $PO_4$ buffer, 8 g NaCl, $H_2O$ 1 liter, pH to 7.6.
3. PBS/BSA: PBS plus 1% bovine serum albumin.
4. Biotinylated Antibody(BA): ABC kit, 1 drop BA in 20 ml PBS/BSA.
5. Avidin Biotin Complex, ABC stain: ABC kit, 2 drops, Avidin DH, 2 drops Biotin-peroxidase, 10 ml PBS/BSA.
6. Diaminobenzidine substaate, DAB: 5 mg diaminobenzidine tetrahydrochloride, 10 ml PBS, 0.004 ml 30% $H_2O_2$.
7. 0.3% $H_2O_2$ in methanol: 0.1 ml 30% $H_2O_2$ in 10 ml.
8. ABC kit purchased from Vector Laboratories, Burlingame, CA.
9. Adriamycin purchased from Adria Laboratories, Inc., Columbus, OH.

II. Immunostaining procedure

Monoclonal antibodies (diluted 1:1000 in PBS/BSA) were used Immunostaining procedure uses modified method of vectastain ABC immunoperoxidase staining procedure, briefly 1. Culture plates were added antibody of cardiac myosin before 3 hr. for staining. Then culture plates continuous incubated at 3 hr. at 37° C.
2. Rinse cell culture plates in CMF saline.
3. Fix sections for 5 min. in 50% methanol and 50% acetone.
4. Rinse 3 times in methanol.
5. Incubate sections for 10 min. in 0.3% $H_2O_2$ in methanol
6. Incubate sections for 30 min. in BA antibody solution.
7. Rinse sections in PBS for 5 min. with 2 times.
8. Incubate sections in ABC stain for 1 hr.
9. Rinse sections in PBS for 5 min. with 3 times.
10. Incubate sections in DAB-peroxide substrate solution for 5 min.
11. Rinse sections for 10 min. in water.
12. Counter-stain for 30 sec. in 1% aqueous fast green, soak in distilled water with 3 times.
13. Air dry cell cultures.

Cell determined by recording the color and the number of microscopic fields (250×). Normal cell is light green and dead cell is brown or very dark green.

Results

The influence of PDI on adriamycin induced damage of chick myocardial cell:

After chick myocardial cell was put into culture for 4 days, Adriamycin was added and remained in culture for 24 hours. Then ABC immunoperoxidase was used for determine survival rate. Under the above condition PDI can clearly be shown to increase the survival rate of chick myocarcial cell.

TABLE 3

The influence of PDI on the survival rate of myocardial cell

Chick myocardial cell was put in culture for 4 days. Then Adriamycin was added. The concentration of each dish was 10 μg Adriamycin/ml medium. In the PDI group, PDI was added. In the Adriamycin group, equal value CMF solution was added. After 24 hours the survival rate was determined.

| | Survival rate (living/total × 100%) |
|---|---|
| Adriamycin (10 μ) | 36.3 ± 3.1 (*16) |
| Adriamycin (10 μ) + PDI | 61.0 ± 3.0 (*15) |
| | P 0.001 |

*indicate number of sampling
Concentration of PDI is 150 μg/ml

EXAMPLE 7

Effects of PDI on hemopoietic system

Effects of PDI on hemopoietic systemm were investigated. Results showed that PDI (ip) could markedly improve the recovery rate of hemopoieses in treatment mice by cyclophosphamide.

With increased nucleated cells in bone-marrow (BMC), endogenous colonies in spleen and higher $^3$H-TdR uptake in marrow and spleen. The level of serum colony stimulating factor (CSF) increased after injection. It is found that PDI protect the stem cells of bone marrow in mice from the killing effect of cyclophosphamide.

Method of animal model is regular which is not part of this invention. Pharmacological effects as illustrated by the following table: by means of the spleen colony assay technique the action of PDI on bone marrow stem cells (CFU-S).

TABLE 4

| Group | Number of sample | Mean CFU-S ± SD | P |
|---|---|---|---|
| Control | 10 | 10.0 ± 0.81 | — |
| Cyclophosphamide | 10 | 4.0 ± 0.71 | <0.001 |
| PDI + Cyclophosphamide | 10 | 7.7 ± 0.80 | >0.05 |

Experimental procedure

Male mice weight 18-20 g were used in the experiments and were divided into treated (PDI) and control groups. The dosage of PDI is 5.5 mg/kg injected intraperitoneally. The control mice were injected with same volume of normal saline. These injections were repeated daily for 3 days. On the last day, both treated and control group were injected intraperitoneally with cyclophosphamide. The dosage of cyclophosphamide is 4.5 mg/kg.

The same experimental procedure for example 8, 9, and 10 in testing mice was used.

EXAMPLE 8

The effect of PDI on phagocytosis of peritoneal macrophage of mice

Method

Add 0.02 ml of 5% washed chick red blood cell suspension to 0.5 ml of the peritoneal exudate, shake gently to mix and incubate at 37° C. for 5 minutes. dip two cover-slips, close to each other, in the above mixture and incubate for 30 minutes for the mmigration of the macrophages along the cover slips, Fix and stain with Sharma stain. Examine microscopically for:

Phagocytic rate—number of macrophages with phagocytized chick red blood cells per 100 macrophages counted.

Method of animal model is regular.

Results

Pharmacological effects as illustrated by the following table.

TABLE 5

| Groups | Number of sample | Phagocytic rate ± SD (%) | P |
|---|---|---|---|
| Control | 10 | 35.10 ± 2.01 | — |
| Cyclophosphamide | 10 | 8.00 ± 0.36 | <0.001 |
| Cyclophosphamide + PDI | 10 | 33.00 ± 1.14 | >0.05 |

*concentration of PDI and cyclophosphamide is the same as example 7.

EXAMPLE 9

The effect of PDI on white blood cells in rats treated by cyclophosphamide

Action of PDI and cyclophosphamide on white blood cells was investigated by means of white blood cells assay. It was revealed that PDI protect white blood cells in rats from the killing effect of cyclophosphamide. Method of testing in animal is standard. The dosage of PDI and cyclophosphamide is the same as in example 7. Time of treatment is 10 days. The results are listed below table:

TABLE 6

| Groups | White blood cells × $10^3$/cm$^3$ ± SD | Number of Sample | P |
|---|---|---|---|
| Normal | 14.6 ± 2.1 | 10 | — |
| Cyclophosphamide | 5.3 ± 1.0 | 10 | <0.001 |
| Cyclophosphamide + PDI | 12.0 ± 1.8 | 10 | >0.05 |

EXAMPLE 10

The effect of PDI on lymphoblastoid trasformation

By means of $^3$H-TdR liquid scintillation assay technique, the action of PDI on lymphoblastoid transformation was investigated.

Method (1) Experimental procedure of animal is the same as in example 7.
(2) Lemphoblastoid tranformation test:
   I. Reagents and conditions for cell culture
      a. Culture media—RPMI 1640, medium 199 minimal essential medium (Eagle).
      b. Buffer—Hepes buffer, the final concentration at 37° C. was 25 mM, to maintain the pH of the medium at 7.31.
      c. Serum—generally 15-20% fetal bovine serum was incorporated, for lymphocytes from mice, 5% was used
      d. Gaseous phase—5% $CO_2$ in air.
      e. Cell concentration—generally 1-2×10$^6$/ml
      f. Stimulants—20 μl/ml for phytohemagglutinin containing polysaccharide (PHA-M) or 10 μl/ml for polysaccharide-free purified phytohemagglutinin (PHA-P).
   II. Measured by liquid scintillation
      a. The conditions of cell culture are same as above. $^3$H-TdR was added after 48 hours of incubation at a final concentration of 1 μCi/ml and continue the incubation for 24 hours.

b. Wash the cells twice with cold normal saline and the erythrocytes were lysed by addition of distilled-water and equal volume of 3.6% NaCl was then added. The intact lymphocytes were again washed once with cold saline. Spin down the lymphocytes and add 2 ml of 10% trichloroacetic acid to precipitate the protein. Wash twice with normal saline. Add 2 ml of ethanol:ether (1:1) to wash once. 0.2 ml of formic acid was then added for digestion till the precipitate was dissolved.

c. Add 4 ml of scintillation fluid to 0.1 ml of the final sample and count in a liquid scintillation counter.

Results are listed in the following table: (concentration of PDI and cyclophosphamide used is the same as that of example 7.)

TABLE 7

| Groups | Number of sample | CPM ± SD | P |
|---|---|---|---|
| Normal | 10 | 1340 ± 51 | — |
| Cyclophosphamide | 10 | 697 ± 38 | <0.001 |
| Cyclophosphamide + PDI | 10 | 1253 ± 50 | >0.05 |

EXAMPLE 11

Toxicity of PDI

1. L.D.$_{50}$: 1321 mg/kg injection in abdomimal cavity in mice.
2. Each dose for an adult is 20 mg. Using 50 kg as the average weight of an adult the dosage is 0.4 mg/kg, therefore it is very safe.

Results and experimental procedure of PDI to overcome toxicity of radiotherapy would be the same as in the examples for chemotherapy.

The embodiment of the invention described here can be modified within the spirit and scope of the present invention. Numerous modifications and variations of the present invention are possible in light of the above teachings.

Having described a pharmaceutical composition referred to as PDI, a process for producing PDI and furthermore described its effect on decreasing side effects of anticancer chemotherapy, radiotherapy and increasing the immune funciton as well as other effects studied by tests carried out by approved procefures, I claim:

1. A process for preparation of ferulic acid comprising:
    a. extracting dried powder of a plant selected from the group consisting of Levisticum officinal Koch and Angelica sinenis Diels with boiling water to yield an extract;
    b. concentrating the extract under reduced pressure;
    c. adding 95% ethanol to said concentrated extract to form a solution;
    d. filtering the solution and concentrating under reduced pressure the resulting filtrate to a syrup;
    e. drying said syrup in the presence of silica gel to form crude ferulic acid;
    f. extracting said crude ferulic acid with 95% ethanol to form an extract;
    g. concentrating said ethanol extract under reduced pressure to yield a residue;
    h. dissolving said residue in water;
    i. passing the water solution through a polyamide column to fractionate the ferulic acid; and
    j. extracting the fractionated ferulic acid with benzolacetone;
    k. distilling the resulting extract under reduced pressure; and
    l. crystallizing ferulic acid therefrom.

2. A process of claim 1, further comprising recrystallizing ferulic acid from chloroform-methanol.

3. A process of claim 1 further comprising steps of extracting the fractionated ferulic acid of step (i) with ethanol, concentrating said 50% ethanol extract under reduced pressure to yield a residue, dissolving the residue in methanol drying the resulting methanol solution with silica gel, and passing the methanol solution through the column.

4. A process of claim 1 wherein the reduced pressure is about 17 mm Hg absolute.

* * * * *